United States Patent [19]

Solyntjes et al.

[11] Patent Number: 5,413,267
[45] Date of Patent: May 9, 1995

[54] SURGICAL STAPLER WITH SPENT CARTRIDGE SENSING AND LOCKOUT MEANS

[75] Inventors: Alan J. Solyntjes, Richfield; Robert M. Eyerly, Lino Lakes, both of Minn.

[73] Assignee: United States Surgical Corporation, Norwalk, Conn.

[21] Appl. No.: 699,718

[22] Filed: May 14, 1991

[51] Int. Cl.$^6$ .................................. A61B 17/068
[52] U.S. Cl. .................................. 227/176; 227/19; 227/178
[58] Field of Search .............. 227/8, 19, 121, 175, 227/176, 177, 178, 179, 180

[56] References Cited

U.S. PATENT DOCUMENTS

| | | |
|---|---|---|
| D. 283,733 | 5/1986 | Rawson et al. . |
| D. 322,143 | 12/1991 | Spreckelmeier . |
| 2,174,219 | 9/1939 | Balma . |
| 2,246,647 | 6/1941 | Vancura . |
| 3,079,606 | 3/1963 | Bobrov et al. . |
| 3,490,675 | 1/1970 | Green et al. . |
| 3,494,533 | 2/1970 | Green et al. ............ 227/19 |
| 3,499,591 | 3/1970 | Green . |
| 3,675,688 | 7/1972 | Bryan et al. . |
| 3,692,224 | 9/1972 | Astafiev et al. . |
| 3,735,762 | 5/1973 | Bryan et al. . |
| 3,795,034 | 3/1974 | Strekopytov et al. . |
| 3,844,289 | 10/1974 | Noiles . |
| 3,873,016 | 3/1975 | Fishbein . |
| 4,006,786 | 2/1977 | Speicher . |
| 4,086,926 | 5/1978 | Green et al. ............ 128/334 R |
| 4,108,306 | 8/1978 | Samuels et al. . |
| 4,202,479 | 5/1980 | Razgulov et al. . |
| 4,202,480 | 5/1980 | Annett . |
| 4,256,251 | 3/1981 | Moshofsky . |
| 4,296,881 | 10/1981 | Lee . |
| 4,304,236 | 12/1981 | Conta et al. . |
| 4,305,539 | 12/1981 | Korolkov et al. . |
| 4,319,576 | 3/1982 | Rothfuss . |
| 4,331,276 | 5/1982 | Bourque . |
| 4,349,028 | 9/1982 | Green . |
| 4,354,628 | 10/1982 | Green ................... 227/19 |
| 4,383,634 | 5/1983 | Green . |
| 4,391,401 | 7/1983 | Moshofsky . |
| 4,415,112 | 11/1983 | Green . |

(List continued on next page.)

FOREIGN PATENT DOCUMENTS

| | | |
|---|---|---|
| 54764/86 | 9/1986 | Australia . |
| 54765 | 9/1986 | Australia . |
| 0373762 | 6/1989 | European Pat. Off. . |
| 0324638 | 7/1989 | European Pat. Off. . |
| 0380025 | 8/1990 | European Pat. Off. . |
| 0489436A1 | 6/1992 | European Pat. Off. . |
| 2744824 | 2/1980 | Germany . |
| 2070499 | 9/1981 | United Kingdom . |
| 8302247 | 7/1983 | WIPO ................ 227/127 |

OTHER PUBLICATIONS

"Auto Suture® Premium Poly CS ™-57 Disposable Surgical Stapler", printed Jul. 1986, reprinted 1990.
"Auto Suture® Poly CS ™-57 Disposable Surgical Stapler", printed Jul. 1988.
"Auto Suture® Poly CS ™-57 Disposable Loading Units with Lactomer® Absorbable Copolymer Staples", printed Jul. 1988.
Flickinger et al. Surgical Stapling *Gastric and Small Bowel Procedures* pp. 1–14.
Anderson et al. Surgical Stapling *Thoraci, Vascular and Esophageal Procedure* pp. 1–101.
Brolin et al. Surgical Stapling *Bariatric Procedures for Morbid Obesity* pp. 1–115.
"Disposable EEA Surgical Stapler and Curved Disposable EEA Surgical Stapler" Information Booklet, printed Jan. 1985.

*Primary Examiner*—Rinaldi I. Rada

[57] ABSTRACT

A stapler is disclosed that includes a mechanism for sensing whether the stapler is loaded with a fired cartridge housing and for preventing the stapler from being closed or fired when loaded with the fired cartridge. The mechanism also prevents the stapler from firing or clamping on tissue when the stapler is not loaded with a staple cartridge.

37 Claims, 8 Drawing Sheets

U.S. PATENT DOCUMENTS

| | | |
|---|---|---|
| 4,429,695 | 2/1984 | Green . |
| 4,442,964 | 4/1984 | Becht . |
| 4,473,077 | 9/1984 | Noiles et al. . |
| 4,480,640 | 11/1984 | Becht . |
| 4,500,025 | 2/1985 | Skwor . |
| 4,506,670 | 3/1985 | Crossley . |
| 4,508,253 | 4/1985 | Green . |
| 4,519,532 | 5/1985 | Foslien . |
| 4,520,817 | 6/1985 | Green . |
| 4,523,695 | 6/1985 | Braun et al. . |
| 4,527,724 | 7/1985 | Chow et al. ............................ 227/8 |
| 4,530,453 | 7/1985 | Green . |
| 4,540,110 | 9/1985 | Bent et al. . |
| 4,556,058 | 12/1985 | Green . |
| 4,568,009 | 2/1986 | Green . |
| 4,569,346 | 2/1986 | Poirier . |
| 4,576,165 | 3/1986 | Green et al. . |
| 4,576,167 | 3/1986 | Noiles . |
| 4,589,582 | 5/1986 | Bilotti . |
| 4,591,085 | 5/1986 | DiGiovanni . |
| 4,592,498 | 6/1986 | Braun et al. . |
| 4,597,517 | 7/1986 | Wagdy . |
| 4,605,004 | 8/1986 | DiGiovanni et al. . |
| 4,606,344 | 8/1986 | di Giovanni . |
| 4,606,345 | 8/1986 | Dorband et al. . |
| 4,607,636 | 8/1986 | Kula et al. . |
| 4,608,981 | 9/1986 | Rothfuss et al. . |
| 4,612,933 | 9/1986 | Brinkerhoff et al. . |
| 4,617,928 | 10/1986 | Alfranca . |
| 4,633,861 | 1/1987 | Chow et al. . |
| 4,633,874 | 1/1987 | Chow et al. . |
| 4,646,745 | 3/1987 | Noiles . |
| 4,664,305 | 5/1987 | Blake, III et al. . |
| 4,665,916 | 5/1987 | Green . |
| 4,684,051 | 8/1987 | Akopov et al. . |
| 4,714,187 | 12/1987 | Green ................................. 227/19 |
| 4,715,520 | 12/1987 | Roehr, Jr. et al. . |
| 4,728,020 | 3/1988 | Green et al. ........................... 227/19 |
| 4,741,336 | 5/1988 | Failla et al. . |
| 4,807,628 | 2/1989 | Peters et al. . |
| 4,809,898 | 3/1989 | Gassner et al. . |
| 4,850,355 | 7/1989 | Brooks et al. . |
| 4,863,088 | 9/1989 | Redmond et al. ..................... 227/19 |
| 4,869,415 | 9/1989 | Fox . |
| 4,881,544 | 11/1989 | Green et al. . |
| 4,881,545 | 11/1989 | Isaacs et al. . |
| 4,892,244 | 1/1990 | Fox et al. .............................. 227/8 |
| 4,915,100 | 4/1990 | Green . |
| 4,938,408 | 7/1990 | Bedi et al. ............................ 227/8 |
| 4,941,623 | 7/1990 | Pruitt .................................. 227/19 |
| 4,955,959 | 9/1990 | Tompkins et al. ................... 227/178 |
| 5,031,814 | 7/1991 | Tompkins et al. . |
| 5,040,715 | 8/1991 | Green et al. . |
| 5,065,929 | 11/1991 | Schulze et al. . |
| 5,071,052 | 12/1991 | Rodak et al. . |
| 5,074,454 | 12/1991 | Peters . |
| 5,083,695 | 1/1992 | Foslien et al. . |
| 5,100,042 | 3/1992 | Gravener et al. . |
| 5,106,008 | 4/1992 | Tompkins et al. . |
| 5,129,570 | 7/1992 | Schulze et al. . |

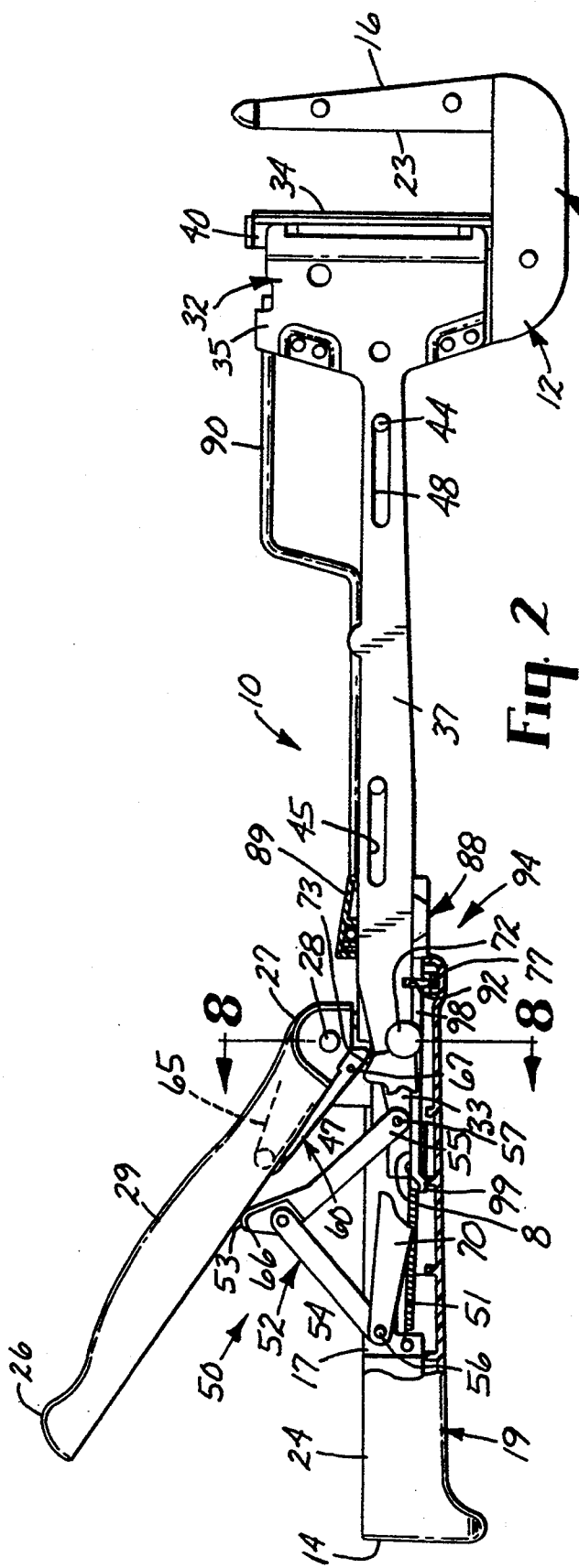

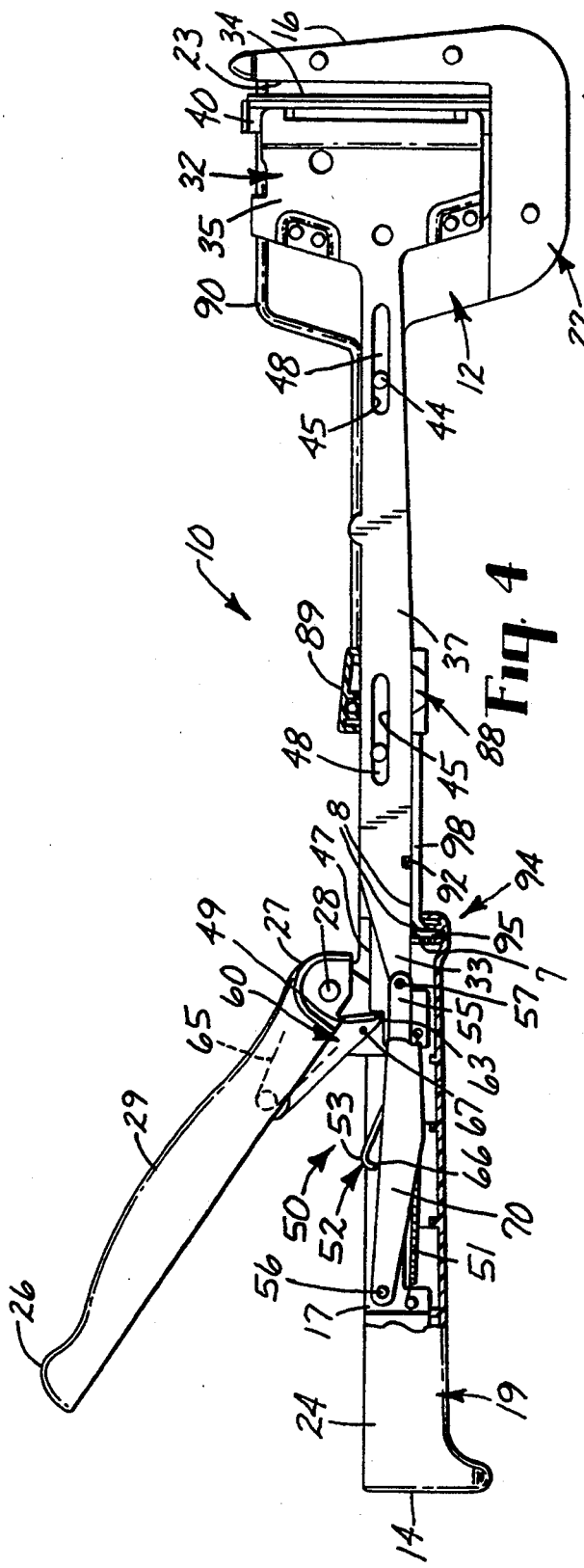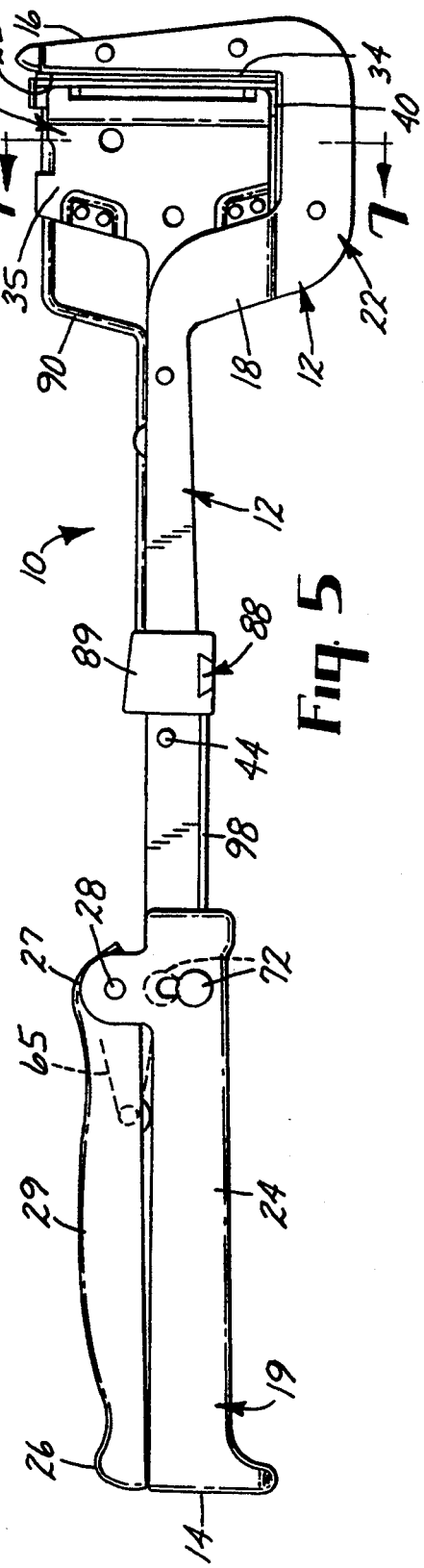

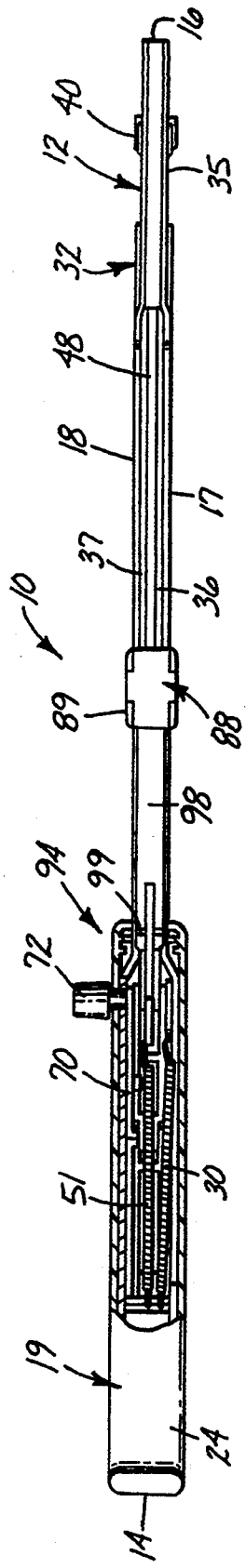
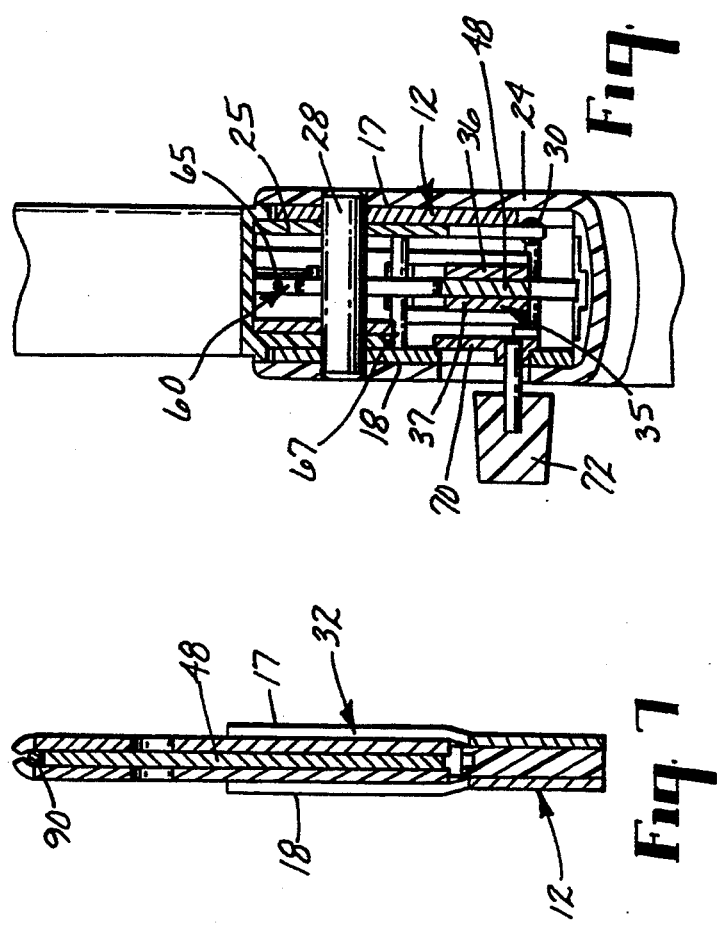
Fig. 6
Fig. 8
Fig. 7

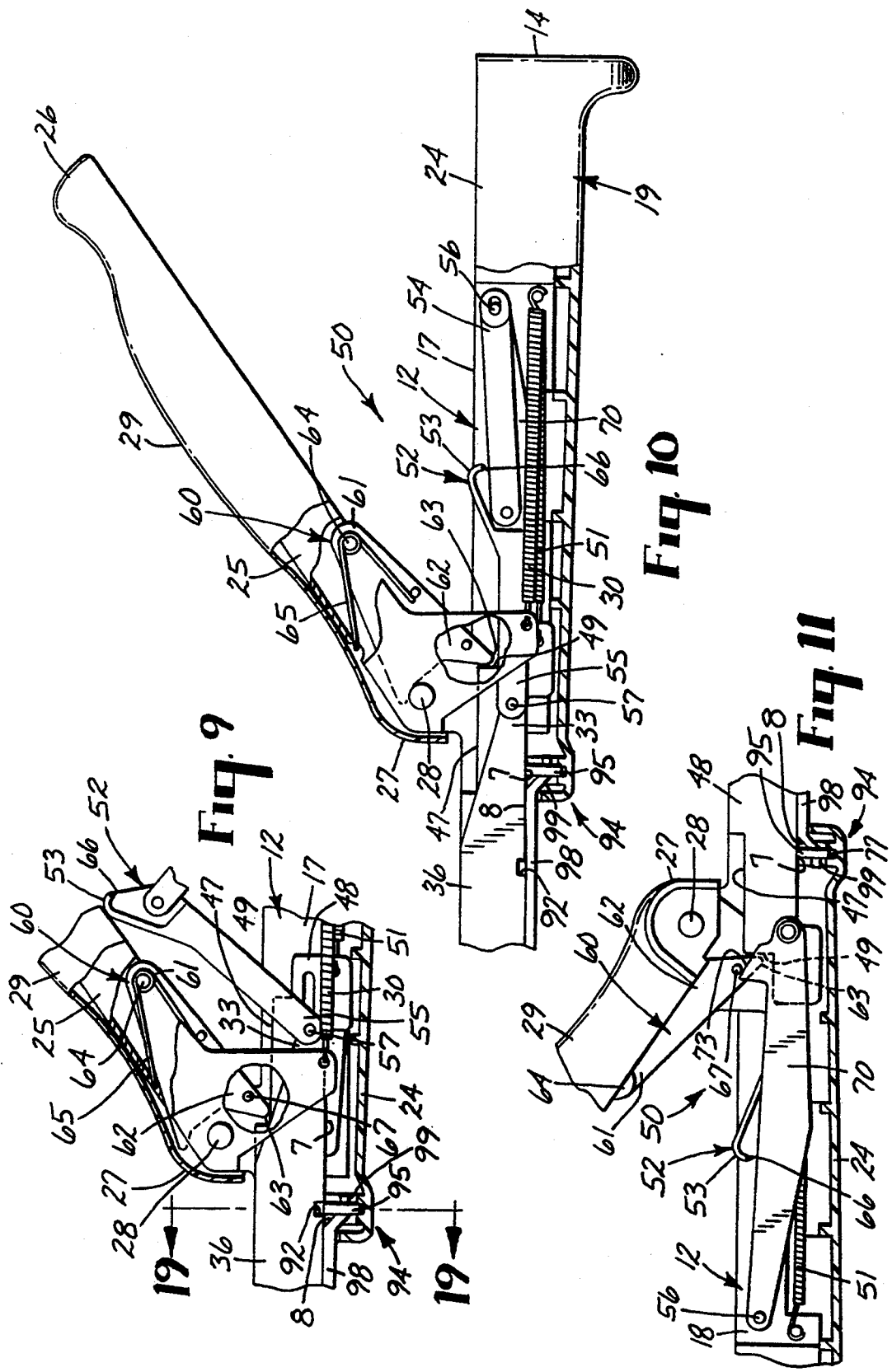

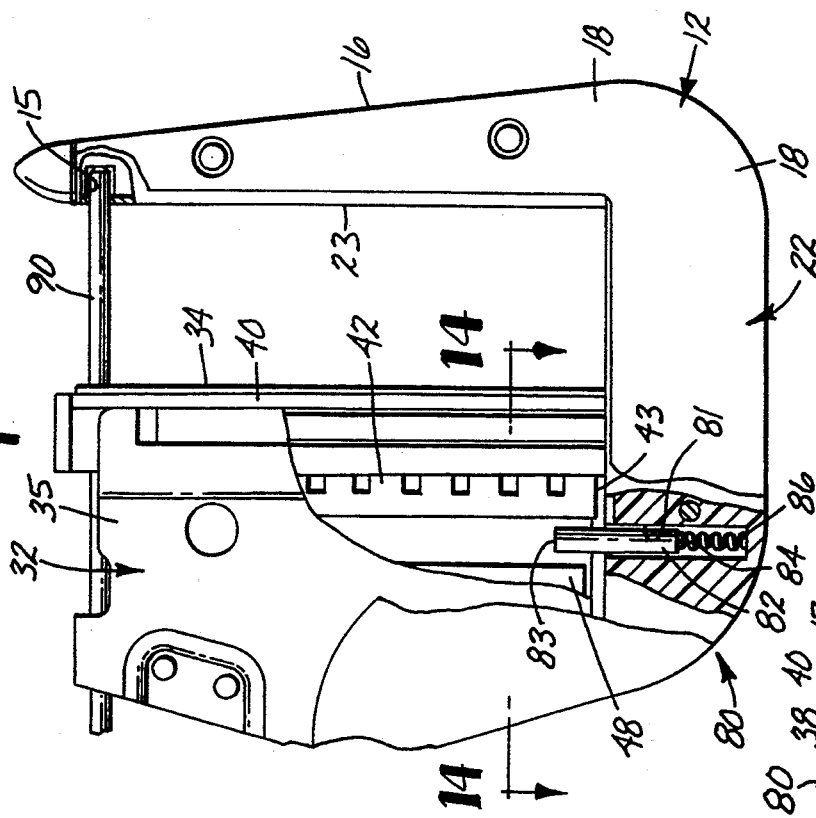
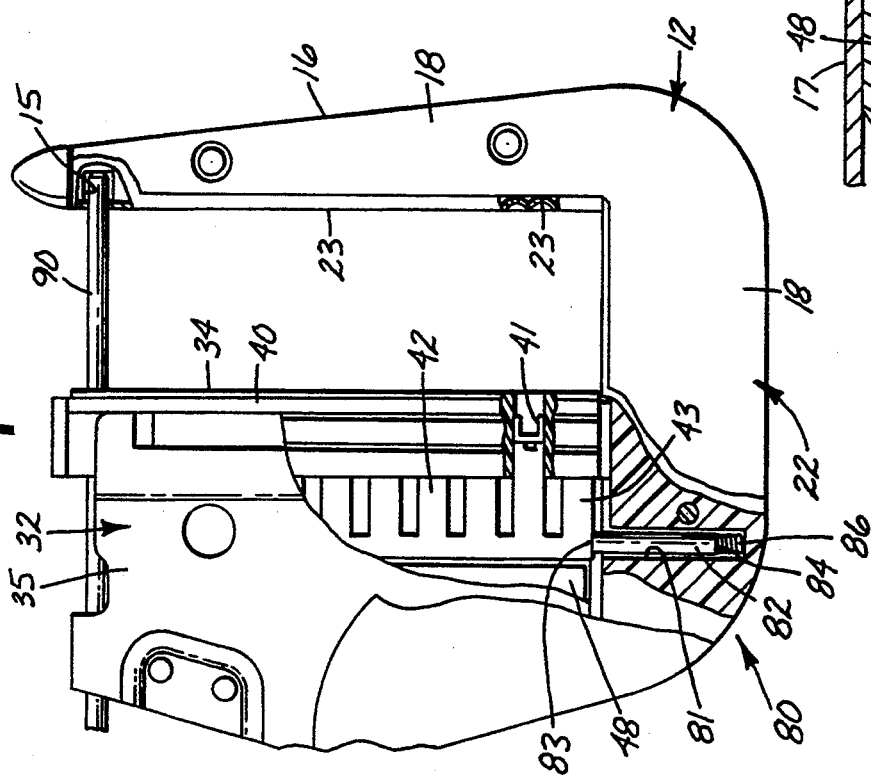
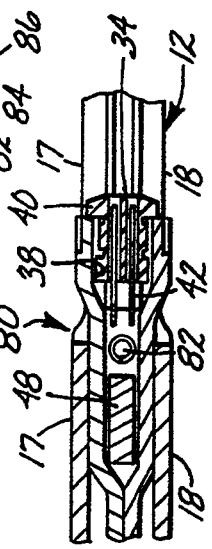

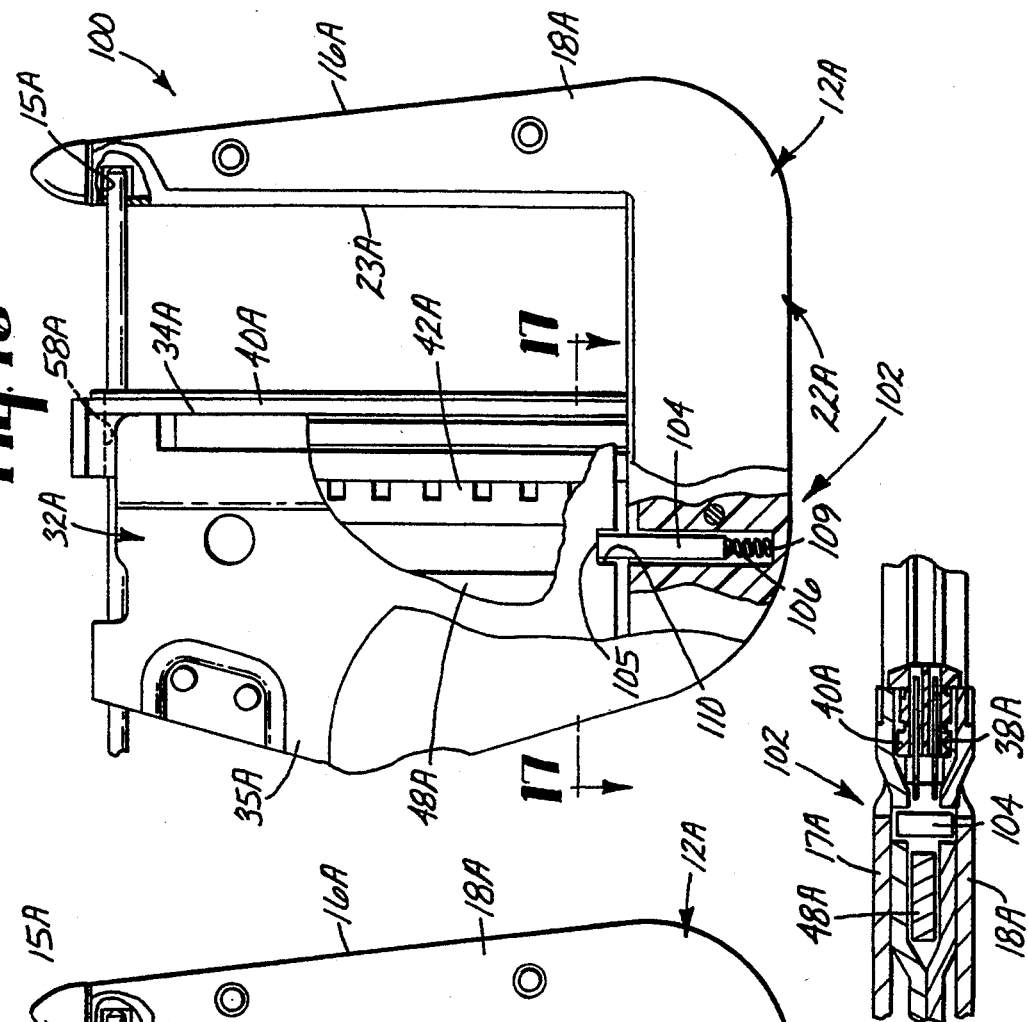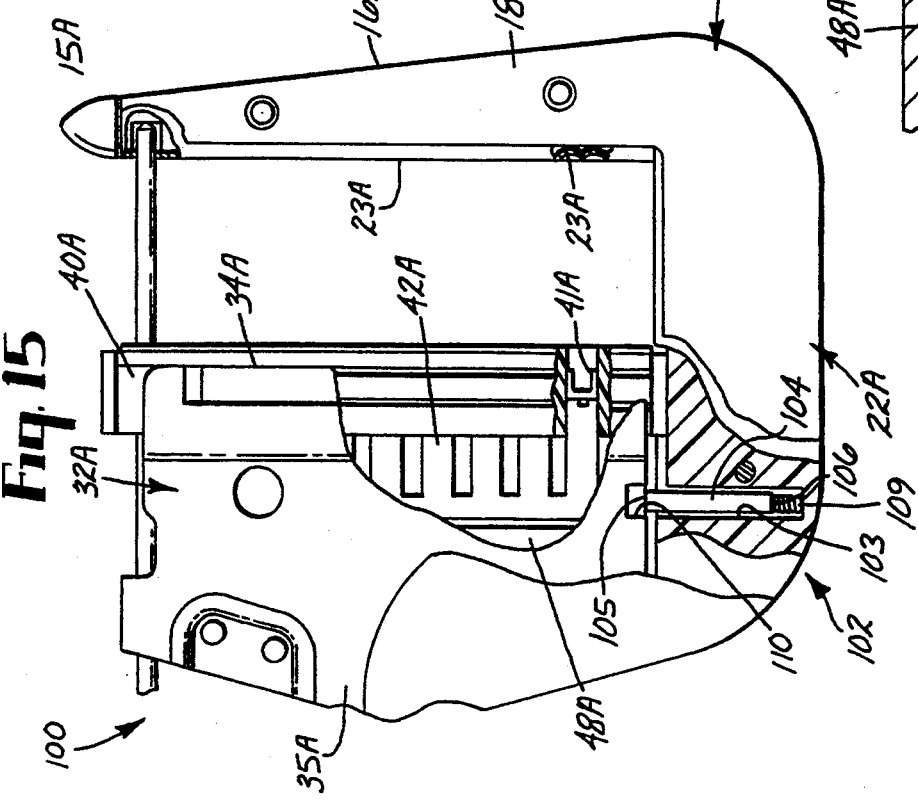

SURGICAL STAPLER WITH SPENT CARTRIDGE SENSING AND LOCKOUT MEANS

TECHNICAL FIELD

The present invention relates generally to surgical stapling instruments and more particularly to the type of surgical stapling instruments used for applying linear parallel rows of staggered staples through compressed living tissue.

BACKGROUND ART

Surgical stapling instruments used for applying parallel rows of staples through compressed living tissue are well known in the art, and are commonly used for closure of tissue or organs prior to transection, prior to resection, or in anastomoses, and for occlusion of organs in thoracic and abdominal plasty procedures. One known pneumo-intestinal surgical stapling instrument of this type has been in use for many years, and is currently available under the trade designation "The PI Stapler", catalog #3960 by Minnesota Mining and Manufacturing Company (3M), St. Paul, Minn., the use of which stapler is described in a publication entitled "Surgical Stapling, Gastric and Small Bowel Procedures, Volume I" ISBN 0-937433-00-4, Library of Congress Catalog Number 85-082599 available from Minnesota Mining and Manufacturing Company (3M), St. Paul, Minn., the contents of which are herein incorporated by reference. That stapler and a similar stapler described in Freund et al. PCT Application No. WO 83/02247, published Jul. 7, 1983 are adapted for firing staples into compressed living tissue from a staple filled cartridge. The staplers have anvil and jaw portions, a cartridge holder including a removable cartridge and a handle lever.

Typically, a "PI" type stapler is positioned adjacent the tissue to be stapled, the anvil and jaw portions are approximated adjacent the tissue to be stapled, and the stapler is clamped on the tissue by moving the handle lever in a first movement to cause the cartridge holder to move toward the anvil placing the cartridge into a staple firing position. Moving the handle lever in a second movement "fires" the stapler (e.g. it ejects the staples from the cartridge).

In some surgical procedures the clamping force results in tissue that is highly compressed to ensure, inter alia, proper hemostasis in the tissues being stapled. The clamping force is present in various degrees in each of the surgical procedures for a "PI" type surgical stapler. Such a clamping force causes tissue trauma in the tissue to be stapled, at least to some degree.

The prior art "PI" type staplers encounter problems because it is difficult to determine when they are loaded with a "spent" cartridge or with a cartridge that does not contain staples. On occasion, a spent cartridge may be inadvertently left in a stapler after it has been fired during a surgical procedure where the stapler is used several times for the same patient, or a spent cartridge may be inadvertently loaded into a stapler that is about to be fired in the patient. If a stapler is loaded with a cartridge housing other than a ready-to-fire cartridge housing and the stapler is clamped on tissue to be stapled, the compressive forces created by the stapler subject the tissue to undesirable and unnecessary trauma. The sequence of (1) clamping the stapler with a spent cartridge on tissue, (2) firing the "dud" stapler (3) subsequently rearming, (4) again approximating the stapler adjacent the tissue to be stapled and (5) reclamping the stapler wastes precious time during the surgical procedure.

Additionally, the prior art "PI" type staplers may be used in procedures in which the surgeon uses a scalpel to manually create an incision on a side of closed staples (e.g. the procedure described in the article entitled "Resection of the Lesion" on pages 14 and 15 of the publication entitled "Surgical Stapling, Gastric and Small Bowel Procedures, Volume I", ISBN 0-937433-00-4, Library of Congress Catalog Number 85-082599 available from Minnesota Mining and Manufacturing Company (3M), St. Paul, Minn.). A spent stapler cartridge used in such procedures may result in unnecessary blood loss, inadequate hemostasis and tissue trauma for the patient undergoing the procedure.

Surgical stapler cartridge safety devices are described in U.S. Pat. Nos. 4,863,088 and 4,955,959, and U.S. patent application Ser. No. 07/629,597. The firing mechanisms in those staplers sequentially close staples into tissue. Since each staple is closed within tissue one after another in succession, the force required to fire such staplers is generally less than the force required to fire a "PI" type stapler where all the staples are generally closed in tissue at the same time.

Unlike the present invention wherein the same part (e.g. a lever or "handle") is operable in both a first movement to approximate and clamp tissue and a second movement to close all the staples within tissue generally simultaneously, the "ILA" type staplers described in U.S. Pat. Nos. 4,863,088 and 4,955,959, and U.S. patent application Ser. No. 07/629,597 utilize separate and distinct member to (1) sequentially fire the staples (e.g. a firing tab or button) and (2) clamp onto the tissue (an element of the stapler that does not include the firing tab or button).

DISCLOSURE OF THE INVENTION

The present invention provides a surgical stapler comprising an anvil frame elongate in a longitudinal direction and including anvil surfaces in a plane generally perpendicular to the longitudinal direction, a cartridge assembly movable relative to the anvil frame between an open position with the cartridge assembly spaced from the anvil surfaces and a closed position with the cartridge assembly and the anvil surfaces in closely spaced relationship. The cartridge assembly comprises a cartridge housing containing a plurality of staples disposed in rows positioned in opposition to the anvil surfaces.

The stapler according to the invention includes a mechanism for firing the stapler by engaging and closing the staples in tissue between the cartridge housing and the anvil surfaces, and a means preventing the cartridge assembly from moving from the open to the closed position unless the stapler is loaded with a ready-to-fire cartridge housing. The means for preventing the cartridge assembly from moving from the open to the closed position (1) prevents approximation and clamping of living tissue between anvil and cartridge components of the stapler when the stapler is loaded with a spent stapler cartridge, (2) prevents the user from attempting to refire the stapler, and (3) provides a stapler that reduces the chances of unnecessary tissue trauma, blood loss, inadequate hemostasis, and squandered time during surgery.

According to a preferred embodiment of the stapler of the present invention, there is provided a stapling instrument comprising an anvil frame having proximal and distal ends and a pair of lateral side portions that are each elongate in a longitudinal direction and spaced to define a channel therebetween. The anvil frame has a handle portion generally adjacent the proximal end with first and second ends, and a jaw portion having anvil surfaces generally adjacent the distal end. The anvil surfaces are positioned in a plane generally perpendicular to the longitudinal direction.

An elongate manually movable handle or lever part having first and second ends is pivotally mounted at its second end to afford pivotal movement of the lever part relative to the anvil frame between a release position with the first end of the lever part being spaced from the first end of the handle portion and an actuation position with the lever part and the handle portion in closely spaced relationship. A biasing means (such as a coil spring mounted at one end to the anvil frame and at the other end to the lever part) biases the lever part toward the release position.

A cartridge assembly having proximal and distal ends is mounted in the channel between the lateral side portions for longitudinal movement relative to the anvil frame. The cartridge assembly comprises a cartridge transporting member having first and second side portions that are each elongate in the longitudinal direction and that are spaced to define a ram channel therebetween. The first and second side portions have surfaces defining a cartridge groove generally adjacent the distal end of the cartridge assembly.

The cartridge groove surfaces are adapted to releasably receive a cartridge housing containing a plurality of staples disposed in rows positioned in opposition to the anvil surfaces, and pusher means, such as a pusher, for pressing the staples within the cartridge housing against the anvil surfaces to engage and close the staples in tissue between the cartridge housing and the anvil surfaces. The pusher has a pair of edges and is positioned proximate the staples for movement between pre-fired and fired positions with the pusher adapted to move distally relative to the cartridge housing when the stapler is fired.

A means mounts the cartridge assembly for longitudinal movement relative to the anvil frame between a closed position with the cartridge housing and the anvil surfaces in closely spaced relationship, and an open position with the cartridge housing and the anvil surfaces spaced farther from each other than in the closed position.

An elongate T-bar or "ram" is mounted in the ram channel between the first and second side portions for longitudinal movement relative to the cartridge transporting member and the anvil frame. The ram is adapted to engage and drive the pusher distally to fire the stapler when the cartridge housing the anvil surfaces are in the closed position.

An actuation means is present to initially move the cartridge assembly from the open to the closed position by a first movement of the lever part from the release to the actuation position and for subsequently firing the stapler (i.e. moving the ram distally relative to the cartridge transporting member to cause the pusher to eject the staples from the cartridge housing, to press the staples against the anvil surfaces and to engage and close the staples in tissues between the cartridge housing and the anvil jaw portion) by a second movement of the lever part from the release to the actuation position. Another biasing means (such as a coil spring connected between the anvil frame and the ram) biases the cartridge assembly from the closed to the open position.

The actuation means preferably comprises a toggle joint linkage having an over center pivoting portion and first and second ends with the first end fixed to the anvil frame and with the second end connected to the cartridge transporting member. The over center pivoting portion preferably has surfaces adapted to engage the lever part when the lever part is first moved from the release to the actuation positions to move the toggle joint linkage from a retracted position past an in-line or centered position with the toggle joint linkage generally straight, to a slightly inverted (relative to the retracted position) extended position to drive the cartridge assembly from the open to the closed positions.

The actuation means also preferably includes means for retaining the cartridge assembly in the closed position against the bias of the coil spring that biases the cartridge assembly from the closed to the open position. Preferably, such a means comprises a stop flange on the over center pivoting portion of the toggle joint linkage that prevents the toggle joint linkage from moving past the extended position. Alternatively such a means may comprise a stop surface located on a handle cover.

The actuation means also preferably includes surfaces defining a cam shoulder surface on the ram, and a pawl having first and second ends and a cam surface generally adjacent the second end of the pawl, and means mounting the pawl on the lever part for movement between a first position with the cam surface generally spaced from the cam shoulder surface on the ram and a second position with the cam surface engaged with the cam shoulder surface on the ram to afford firing of the stapler by driving the ram distally relative to the cartridge transporting member. Also preferably, the stapler further includes means, such as a torsion spring, for biasing the pawl toward the second position, and the ram has surfaces which are adapted to retain the pawl in the first position until the cartridge assembly is moved from the open to the closed position.

Additionally, the stapler preferably further includes a release arm having a first end pivotally mounted to the proximal end of the anvil frame and a second engagement end. The release arm has surfaces adapted to engage the pawl and the toggle joint linkage to move the pawl from the second to the first position and to move the toggle joint linkage from the extended toward the retracted position to afford movement of the cartridge assembly from the closed to the open position under the bias of the means for biasing the cartridge assembly from the closed to the open position (e.g. the coil spring).

The stapler according to the present invention also includes a means for sensing whether the stapler is loaded with a fired cartridge housing and for preventing the stapler from being closed or fired when loaded with the fired cartridge.

In a first embodiment of a stapler according to the present invention, the means for preventing the cartridge assembly from moving from the open to the closed positions when the stapler is loaded with a spent cartridge housing comprises the anvil frame having surfaces defining a safety aperture opening into the surface of the anvil frame and having a bottom surface, and a locking pin having first and second ends. The locking pin is mounted within the safety aperture for movement between a free travel position with the first end of the locking pin abutting an edge of the pusher to afford a single, reciprocating movement of the cartridge assembly between the open and closed positions, and a blocking position with the first end of the locking pin projecting beyond the safety aperture and into the path of the ram to prevent subsequent movement of the cartridge assembly from the open to the closed position.

A biasing means biases the locking pin toward the blocking position. That biasing means preferably comprises a coil spring having a first end connected to the second end of the locking pin and a second end connected to the bottom surface of the safety aperture.

In a second embodiment of stapler according to the present invention, the stapler includes a different means for preventing the cartridge assembly from moving from the open to the closed position when the stapler is loaded with a cartridge housing with the pusher in a fired position comprising a locking notch in the cartridge transport member of the cartridge assembly such that the locking pin engages with the surfaces of the locking notch to prevent movement of the cartridge assembly from the open to the closed position when the locking pin is in the blocking position. In the second embodiment, the locking pin engages the locking notch to prevent movement of the cartridge assembly rather than simply acting as an obstacle to the ram.

In a third embodiment of stapler according to the present invention, the locking notch and/or the locking pin have sloped or ramped camming surfaces to cam the locking pin toward the free travel position when the cartridge assembly initially moves from the open to the closed position.

BRIEF DESCRIPTION OF THE DRAWING

The present invention will be further described with reference to the accompanying drawing wherein like reference numerals refer to like parts in the several views, and wherein:

FIGS. 2 through 5 are enlarged first side views of the surgical instrument of FIG. 1 which sequentially illustrate the operation of the stapler wherein:

FIG. 2 shows the relative positions of the anvil frame and the cartridge assembly in an open position and has portions broken away to show details;

FIG. 3 illustrates the positions of the anvil frame and the cartridge assembly just after the cartridge assembly is moved to the closed position and has portions broken away to show details;

FIG. 4 shows the positions of the anvil frame and the cartridge assembly just before the stapler is fired and has portions broken away to show details;

FIG. 5 illustrates the stapler just after the stapler is fired;

FIG. 6 is an enlarged bottom view of the surgical instrument of FIG. 1 which has portions broken away to show details;

FIG. 7 is an enlarged sectional view of the stapler of FIG. 1 taken approximately along line 7-7 of FIG. 5;

FIG. 8 is an enlarged sectional view of the stapler of FIG. 1 taken approximately along line 8-8 of FIG. 2 and having portions broken away to show details;

FIG. 9 is an enlarged second side view of the stapler of FIG. 1 having portions broken away to show details of an actuation mechanism;

FIG. 10 is an enlarged second side view of the stapler of FIG. 1 having portions broken away to show details of an actuation mechanism and which illustrates the proximal end of the stapler;

FIG. 11 is an enlarged first side view of the stapler of FIG. 1 having portions broken away to show details of an actuation mechanism;

FIG. 12 is an enlarged first side view of the distal end of the stapler of FIG. 1 illustrating a pusher in a pre-fired position;

FIG. 13 is an enlarged first side view of the distal end of the stapler of FIG. 1 illustrating a pusher in a fired position;

FIG. 14 is an enlarged sectional view of the stapler of FIG. 13 taken approximately along line 14—14 of FIG. 13 and having portions broken away to show details;

FIG. 15 is an enlarged first side view of a distal end of a second embodiment of surgical stapler according to the present invention whose proximal end is generally identical to the proximal end of the stapler of FIG. 1, and which illustrates a pusher in a pre-fired position;

FIG. 16 is an enlarged first side view of the distal end of the stapler of FIG. 15 illustrating a pusher in a fired position;

FIG. 17 is an enlarged sectional view of the stapler of FIG. 15 taken approximately along line 17—17 of FIG. 16 and having portions broken away to show details;

DETAILED DESCRIPTION

Figure 1:
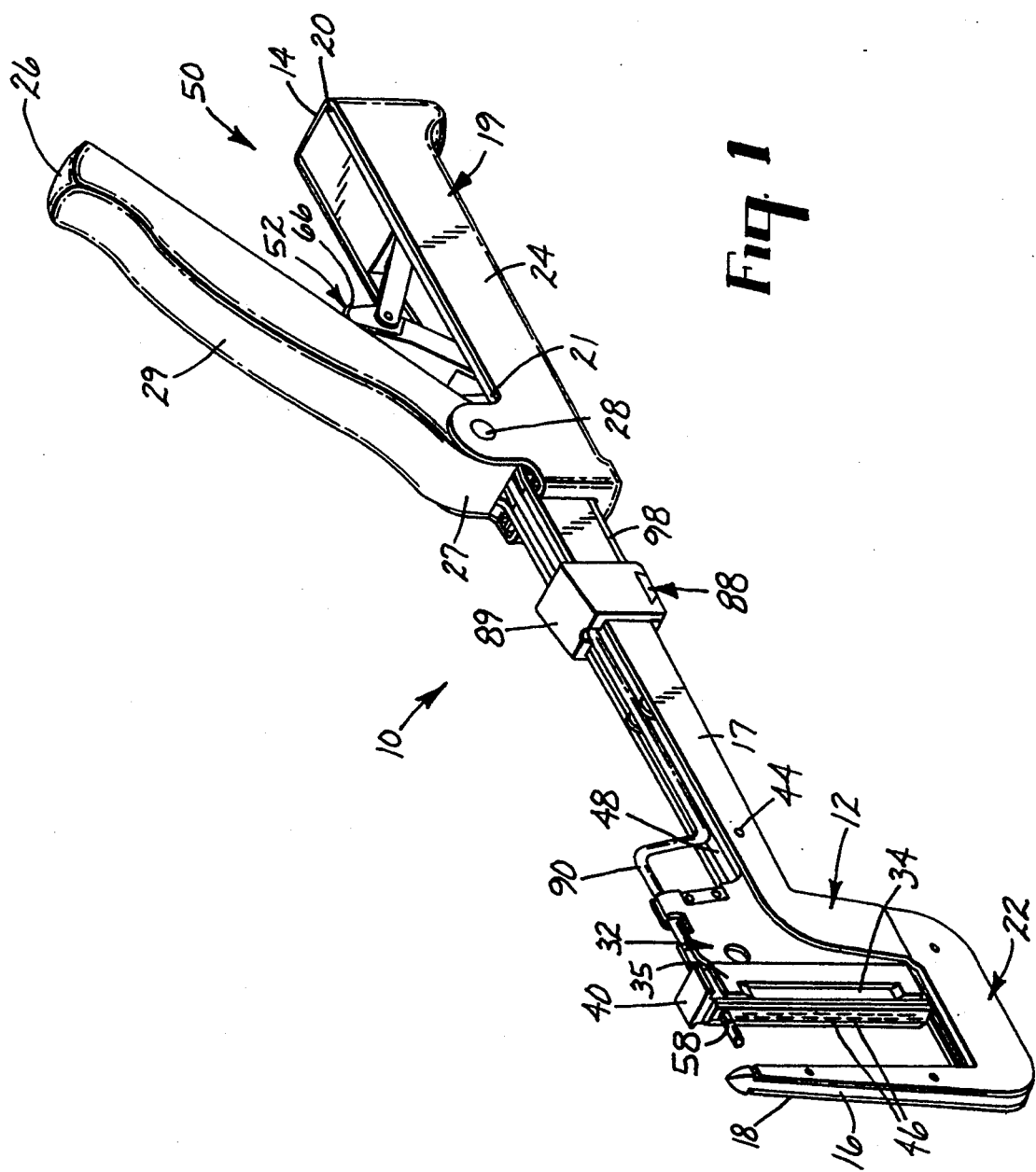
FIG. 1 is a perspective view of the surgical stapling instrument according to the present invention.
Figure 18:
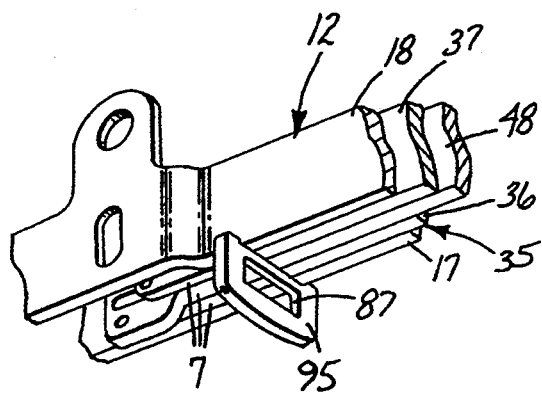
FIG. 18 is an enlarged perspective view of the stapler of FIG. 1 having portions broken away to show detail and showing a safety gate in a latched position.
Figure 19:
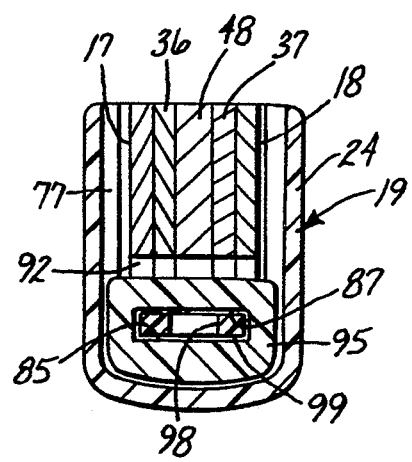
FIG. 19 is a sectional view of the stapler of FIG. 1 taken approximately along line 19—19 of FIG. 9.

Referring now to FIGS. 1 through 14 of the drawing, there is shown a first embodiment of surgical stapling instrument according to the present invention, generally designated by the reference numeral 10.

Generally the surgical stapling instrument 10 comprises an anvil frame 12 having proximal 14 and distal 16 ends and a pair of lateral side portions 17 and 18 that are each elongate in a longitudinal direction and spaced to define a channel therebetween. The anvil frame 12 has a handle portion 19 generally adjacent the proximal end 14 with first 20 and second 21 ends, and a jaw portion 22 having anvil surfaces 23 generally adjacent the distal end 16. The anvil surfaces 23 are specially shaped generally in the form of a "w" and are positioned in a plane generally perpendicular to the longitudinal direction. The jaw portion 22 includes surfaces defining an alignment aperture 15 opening onto the anvil surfaces 23, the function of which will be described later.

A handle housing 24 is attached to the anvil frame 12 and may be constructed from any suitable material such as but not limited to a polymeric material such as nylon, polypropylene, high density polyethylene, acrylonitrile butadiene styrene (ABS), polyetherimide, polystyrene, acetal or polycarbonate.

An elongate manually movable handle or lever part 25 (see FIG. 9) having first 26 and second 27 ends is pivotally mounted at its second end 27 to the anvil frame 12 by means such as a pin 28. A handle cover 29 is attached to the lever part 25 and may be constructed from any suitable material such as but not limited to a polymeric material similar to the material used to construct the handle housing 24. The handle cover 29 and the handle housing 24 are shaped to afford convenient, efficient manual grasping of the stapler 10 and may be snap fit to the stapler 10.

The lever part 25 is connected to the anvil frame 12 at a position generally adjacent the second end 21 of the handle portion 19. The pin 28 mounts the handle part 25 and handle cover 29 to the anvil frame 12 to afford pivotal movement of the lever part 25 relative to the anvil frame 12 between a release position (FIGS. 1, 2 and 4) with the first end 26 of the lever part 25 being spaced from the first end 14 of the handle portion 19 and an actuation position (FIGS. 3 and 5) with the lever part 25 and the handle portion 19 in closely spaced relationship. A biasing means biases the lever part 25 toward the release position. Preferably, the biasing means comprises an extension coil spring 30 mounted at one end to the anvil frame 12 and at the other end to the lever part 25.

A cartridge assembly 32 having proximal 33 and distal 34 ends is mounted in the channel between the lateral side portions 17 and 18 for longitudinal movement relative to the anvil frame 12. The cartridge assembly 32 comprises a cartridge transporting member 35 having first 36 and second 37 side portions that are each elongate in the longitudinal direction and that are spaced to define a ram channel therebetween. The first and second side portions 36 and 37 have surfaces defining a cartridge groove 38 generally adjacent the distal end 34 of the cartridge assembly 32. The cartridge groove surfaces 38 are adapted to releasably receive a cartridge housing 40.

The cartridge housing 40 includes a plurality of staples 41 disposed in rows oriented in planes generally perpendicular to the longitudinal direction and positioned in opposition to the anvil surfaces 23, and manually activatable means, such as a pusher 42, for pressing the staples 41 within longitudinal slots 46 in the cartridge housing 40 against specially shaped anvil surfaces 23 to engage and close the staples 41 in tissue between the cartridge housing 40 and the anvil surfaces 23. The pusher 42 has a pair of edges 43 and is positioned proximate the staples 41 for movement between pre-fired (FIG. 12) and fired (FIG. 13) positions with the pusher 42 adapted to move distally relative to the cartridge housing 40 when the stapler 10 is fired. The cartridge housing 40 also has surfaces defining a close fitting hole or alignment through passage 58 positioned in opposition to the alignment aperture 15 in the anvil frame 12. The alignment through passage 58 and the alignment aperture 15 may be generally cylindrical and coaxial and perform a function to be described later.

A means such as pins 44 and grooves 45 mounts the cartridge assembly 32 for longitudinal movement relative to the anvil frame 12 between a closed position (FIGS. 3, 4 and 5) with the cartridge housing 40 and the anvil surfaces 23 in closely spaced relationship, and an open position (FIGS. 1 and 2) with the cartridge housing 40 and the anvil surfaces 23 spaced farther from each other than in the closed position.

An elongate T-bar or ram 48 is mounted in the ram channel between the first and second side portions 36 and 37 of the cartridge transport member 35 for longitudinal movement relative to the cartridge transporting member 35 and the anvil frame 12. The T-bar or ram 48 is adapted to engage the pusher 42 to drive the pusher 42 distally to eject the staples 41 from the cartridge housing 40, to press the staples 41 against the specially shaped anvil surfaces 23 and to engage and close the staples 41 in tissues between the cartridge housing 40 and the anvil jaw portion 22 when the cartridge housing 40 and the anvil surfaces 23 are in the closed position.

FIGS. 2 through 5 sequentially illustrate the operation of the stapler 10. An actuation means 50 operable in a first movement of the lever part 25 from the release to the actuation position initially moves the cartridge assembly 32 from the open to the closed position (FIGS. 2 and 3). The actuation means 50 is operable in a second movement (FIGS. 4 and 5) of the lever part 25 from the release to the actuation position to subsequently fire the stapler 10 (e.g. the actuation means 50 drives the ram 48 distally relative to the cartridge transporting member 35 to engage and move the pusher 42 distally to eject the staples 41 from the cartridge housing 40, to press the staples 41 against the anvil surfaces 23 and to engage and close the staples 41 in tissues between the cartridge housing 40 and the anvil jaw portion 22). Means such as a coil spring 51 connected between the anvil frame 12 and the ram 48 bias the cartridge assembly 32 from the closed to the open position and is temporarily overcome by the actuation means 50.

The actuation means 50 preferably comprises a toggle joint linkage 52 having an over center pivoting portion 53 and first 54 and second 55 ends with the first end 54 pivotally mounted to the anvil frame 12 by pin 56 and with the second end 55 pivotally connected to the cartridge transporting member 35 by a pin 57. The over center pivoting portion 53 preferably has surfaces adapted to engage cooperable surfaces on the lever part 25 when the lever part 25 is first moved from the release to the actuation position to move the toggle joint linkage 52 from a retracted position (see FIGS. 1 and 2 with the cartridge assembly 32 in the open position) past an in-line or centered position with the toggle joint linkage generally straight (not shown), to an extended position (FIGS. 3, 4, 5 and 10) with the toggle joint linkage 52 being slightly bent in a direction inverted relative to the retracted position. Movement of the toggle joint linkage 52 from the retracted to the extended position drives the cartridge assembly 32 from the open to the closed positions.

The actuation means also preferably includes means for retaining the cartridge assembly 32 in the closed position against the bias of the coil spring 51 for biasing the cartridge assembly 32 from the closed to the open position. Preferably, such a means comprises a stop flange 66 on the over center pivoting portion 53 of the toggle joint linkage 52. The stop flange 66 is adapted to engage surfaces on the toggle joint linkage 52 to prevent the toggle joint linkage 52 from moving past the extended position. Alternatively such a means may comprise a stop surface located on the handle housing 24. Also, a relatively weak torsion spring (not shown) may be mounted on the over center pivoting portion 53 of the toggle joint linkage 52 to bias the toggle joint linkage 52 toward the extended position and to prevent the cartridge assembly from accidentally opening when the handle lever 15 is moved from the actuation to the release position just after firing the stapler 10.

The actuation means 50 preferably includes surfaces defining a cam shoulder surface 49 on the ram 48, and a pawl 60 having first 61 and second 62 ends and a cam surface 63 generally adjacent the second end 62. A means such as pin 64 mounts the pawl 60 on the lever part 25 for movement between a first position (FIGS. 2, 3 and 9) with the cam surface 63 spaced from the cam shoulder surface 49 on the ram 48 and a second position (FIGS. 4, 10 and 11) with the cam surface 63 engaged with the cam shoulder surface 49 on the ram 48 to afford firing of the stapler 10 by driving the ram 48 distally relative to the cartridge transporting member 35 when the cartridge assembly 32 is in the closed position. Also preferably, the stapler 10 further includes means for biasing the pawl toward the second position such as torsion spring 65, and the ram 48 has sliding surfaces 47 adapted to retain the pawl 60 in the first position until the cartridge assembly 32 is moved from the open to the closed position.

Additionally, the stapler 10 includes a release arm 70 having a first end pivotally mounted to the proximal end 14 of the anvil frame 12 by pin 56 and a second end connected to manually activatable release button 72 extending laterally from the handle housing 24. The release arm 70 has surfaces 73 adapted to engage shoulder portions or "pin" 67 of the pawl 60 and laterally inwardly projecting surfaces (not shown) adapted to engage the over center portion 53 of the toggle joint linkage 52 to initially move the pawl 60 from the second toward the first position and to then move the toggle joint linkage 52 from the extended toward the retracted position to afford movement of the cartridge assembly 32 from the closed to the open position under the bias of spring 51. The function of the alignment through passage 58 and the alignment aperture 15 will now be described relative to the function of a safety guide member 88 comprising a sleeve 89 having proximal and distal ends. The sleeve 89 is slidably mounted on the anvil frame 12 for longitudinal movement relative thereto. A longitudinally extending alignment or retention pin 90 is mounted on the distal end of the sleeve 89 for movement between an alignment position (FIGS. 3, 4 and 5) with the alignment pin 90 passing through the cartridge housing alignment through passage 58 and extending into the alignment aperture 15 to position the rows of staples 41 relative to the specially shaped surfaces 23 on the anvil frame 12 to afford a more precisely controlled formation of fired staples and to prevent tissue from escaping from between the cartridge housing 40 and the anvil surfaces 23 when the cartridge assembly 32 is moved to the closed position, and a release position (FIGS. 1 and 2) with the alignment pin 90 spaced from the alignment through passage 58 and the alignment aperture 15 to afford removal and replacement of the cartridge housing with a new cartridge housing.

There may optionally be present means 94 for preventing the cartridge assembly 32 from moving from the open to the closed position unless the alignment pin 90 is in the alignment position, and for preventing the alignment pin 90 from moving from the alignment position toward the release position when the cartridge assembly 32 is in the closed position comprising surfaces defining a safety notch 92 in the cartridge assembly 32 (including both the ram 48 and the cartridge transport member 35) and the anvil frame 12.

The surfaces defining a safety notch 92 in the anvil frame 12, cartridge transport member 35 and ram 48 are aligned when the cartridge assembly 32 is in the open position to define a continuous safety notch (FIGS. 2, 9, 18 and 19) extending laterally across the stapler 10 and are staggered (see FIGS. 3, 4 and 10) when the cartridge assembly 32 is in the closed position.

The means 94 includes a safety gate 95 (FIGS. 18 and 19) having cam shoulder surfaces 85 and return cam surfaces 8 generally opposite the cam surfaces 85. The safety gate 95 includes surfaces defining a safety gate hole 87. The safety gate 95 is mounted adjacent the anvil frame 12 for relative movement thereto between a latched position (FIG. 2) with the safety gate 95 engaged with the surfaces defining the continuous safety notch 92 to prevent relative movement between the cartridge assembly 32 and the anvil frame 12, and an unlatched position (FIGS. 3, 4 and 9) with the safety gate 95 spaced from the safety notch 92 to afford relative longitudinal movement of the cartridge assembly 32 and the anvil frame 12 between the open and closed positions. The handle housing 24 includes guide surfaces defining a slot 77 that affords reciprocating movement of the safety gate 95 between the latched and unlatched positions.

As part of the means 94, the safety guide member 88 includes safety gate deactivating guides 98 projecting proximally from the proximal end of the sleeve 89 and through the safety gate hole 87. The return cam surfaces 8 of the guides 98 bias the safety gate 95 toward the latched position when the alignment pin 90 is in a position other than the alignment position. The cam surfaces 99 at a proximal end of the guides 98 are adapted to engage the cam shoulder surfaces 85 of the safety gate 95 to drive the safety gate 95 from the latched to the unlatched position when the alignment pin 90 is moved to the alignment position. Surfaces 7 (FIG. 18) on the cartridge transport member 35 and ram 48 are adapted to engage the "top" of the safety gate 95 to prevent the return cam surfaces 8 from driving the safety gate 95 from the unlatched position toward the latched position when the cartridge assembly is in the closed position. Thus, once the alignment pin 90 is moved to the aligned position, the means 94 also prevents the alignment pin 90 from moving from the alignment position toward the release position when the cartridge assembly 32 is in the closed position.

The stapler 10 according to the present invention also includes a means preventing the cartridge assembly from moving from the open to the closed position unless the stapler 10 is loaded with a ready-to-fire staple cartridge. As best seen in FIGS. 12 though 14, a first embodiment of a stapler 10 according to the present invention may comprise a means for preventing the cartridge assembly 32 from moving from the open to the closed positions when the stapler 10 is loaded with a cartridge housing 40 having a pusher 42 in a fired position. Such a means prevents approximation and clamping of living tissue between anvil (e.g. 23) and cartridge (e.g. 40) components of the stapler 10 when the stapler 10 is loaded with a spent stapler cartridge, and prevents firing of the stapler 10 when the stapler is loaded with a spent stapler cartridge.

FIGS. 12 through 14 illustrate a stapler 10 wherein the means for preventing the cartridge assembly 32 from moving from the open to the closed positions comprises the anvil frame 12 having surfaces defining a safety aperture 81 opening into the surface of the anvil frame 12 and having a bottom surface, and a locking plate or pin 82 having first 83 and second 84 ends. The locking pin 82 is mounted within the safety aperture 81 for movement between a free travel position (FIG. 12) with the first end 83 of the locking pin 82 generally abutting an edge 43 of the pusher 42 to afford a single, reciprocating movement of the cartridge assembly 32 between the open and closed positions, and a blocking position (FIG. 13) with the first end 83 of the locking pin 82 projecting beyond the safety aperture 81 and into the path of the ram 48 to prevent movement of the cartridge assembly 32 from the open to the closed position. A biasing means biases the locking pin 82 toward the blocking position. That biasing means preferably comprises a coil spring 86 having a first end connected to the second end 84 of the locking pin 82 and a second end connected to the bottom surface of the safety aperture 81.

OPERATION

The operation of the present invention may now be described with reference to the stapler 10. FIGS. 2 through 5 sequentially illustrate the operation of the stapler 10.

FIG. 2 illustrates the relative positions of the anvil frame 12 and the cartridge assembly 32 in an open position. Typically the stapler 10 may be positioned adjacent the tissue to be stapled, and the alignment pin 90 is then moved from the release position (FIG. 2) to the alignment position (FIGS. 3, 4 and by moving the sleeve 89 distally. When the alignment pin 90 is located in the alignment position, the cam surfaces 99 move the safety gate 95 to the unlatched position to afford relative movement between the cartridge assembly 32 and the anvil frame 12.

In the alignment position, the alignment pin 90 passes through the cartridge housing alignment through passage 58 and extends into the alignment aperture 15 to orient and position the rows of staples 41 relative to the specially shaped surfaces 23 on the anvil frame 12 to afford a more precisely controlled formation of fired staples. Placing the alignment pin 90 in the alignment position also prevents tissue from escaping from between the cartridge housing 40 and the anvil surfaces 23 when the cartridge assembly 32 is moved to the closed position.

FIG. 3 illustrates the positions of the anvil frame 12 and the cartridge assembly 32 just after the cartridge assembly 32 is moved to the closed position by a first movement of the lever part 25 from the release position to the actuation position, after which the coil spring 30 returns the lever part 25 to the release position shown in FIG. 4. When the cartridge assembly is in the closed position, the surfaces 7 (FIG. 18) on the cartridge transport member 35 and ram 48 are adapted to engage the "top" of the safety gate 95 and prevent the return cam surfaces 8 from driving the safety gate 95 from the unlatched position toward the latched position. Thus, once the alignment pin 90 is moved to the aligned position as shown in FIG. 3, the means 94 also prevents the alignment pin 90 from moving from the alignment position toward the release position when the cartridge assembly 32 is in the closed position. This feature prevents a user from (1) clamping the stapler 10 on the tissue to be stapled and (2) thereafter moving the alignment pin 90 from the alignment position.

FIG. 4 shows the positions of the anvil frame 12 and the cartridge assembly 32 just before the stapler 10 is fired. After the cartridge assembly 32 is moved to the closed position, the pawl 60 moves to the second position with the cam surface 63 generally engaged with the cam shoulder surface 49 of the ram 48. In this position, the stapler 10 is ready to be fired. A second movement of the lever part 25 from the release position to the actuation position (FIG. 5) causes the ram 48 to move distally relative to the cartridge transport member 35 and the anvil frame 12, which drives the pusher 42 distally to eject the staples 41 from the cartridge housing 40 to press the staples 41 against the specially shaped anvil surfaces 23 and to engage and close the staples 41 in tissues between the cartridge housing 40 and the anvil jaw portion 22.

Once the cartridge assembly 32 is moved to the closed position, the spring 51 biases the cartridge assembly toward the open position but is prevented from moving the cartridge assembly 32 to the open position by engagement between a stop flange 66 of the toggle joint linkage 52 with another portion of the toggle joint linkage 52 generally adjacent the over center pivoting portion 53. Optionally, engagement between the toggle joint linkage 52 and surfaces on the handle housing 24 may prevent further movement of the toggle joint linkage 52. A torsion spring (not shown) prevents the toggle joint linkage from accidentally "popping-up" or returning to the retracted position when the stapler 10 is fired.

After the stapler 10 is fired, the user may control the return of the cartridge assembly 32 to the open position by moving manually activatable release button 72 "upward" to engage surfaces 73 of release arm 70 with shoulder portions or pin 67 of the pawl 60 and to engage laterally inwardly projecting surfaces (not shown) on the arm 70 with the over center portion 53 of the toggle joint linkage 52 to move the pawl 60 from the second toward the first position and to move the toggle joint linkage 52 from the extended toward the retracted position against the bias of the torsion spring (not shown). Such a movement of the release arm 70 allows the spring 51 to return the cartridge assembly 32 to the open position.

Once the cartridge assembly 32 is moved to the open position, the return cam surfaces 8 are free to drive the safety gate 95 into engagement with the safety notch 92 to prevent the cartridge assembly 32 from moving from the open to the closed position unless the alignment pin 90 is again moved to the alignment position. Thus, this feature operates continuously, even if the stapler is subsequently reused in the same patient.

As best seen in FIG. 13, after the stapler 10 is fired and the cartridge assembly 32 is moved to the open position, the pusher 42 is located closer to the cartridge housing 40 than in the pre-fired position so that the second end of pin 82 no longer engages the edge 43 of pusher 42. Thus after the ram 48 moves back to the open position, the spring 86 biases the pin 82 from the free-travel to the blocking position with the first end 83 of the locking pin 82 projecting beyond the safety aperture 81 and into the path of the ram 48 to thereby prevent movement of the cartridge assembly 32 from the open to the closed position. It should be pointed out that the pin 82 will not only prevent the stapler 10 from firing when loaded with a spent cartridge, but will also prevent the firing of the stapler 10 when the stapler is not loaded with a cartridge housing 40 at all.

Also, the pin 82 prevents firing of the stapler 10 should the fired cartridge housing be replaced with another fired cartridge, since the edge portion of the pusher of the fired cartridge would not be able to move the pin 82 from the blocking to the free-travel position. The stapler 10 can be refired only by replacing the fired cartridge housing with an unfired or ready-to-fire cartridge housing 40 having an edge surface 43 of the pusher 42 in the proper position to move the pin 82 to the free-travel position.

It should be noted that the mechanical advantage provided by the toggle joint linkage 52 is at its minimum when the cartridge assembly 32 is in the open position and generally increases as the cartridge assembly 32 moves toward the closed position. Thus, it is important to prevent the cartridge assembly 32 from moving from the open toward the closed position to thereby minimize the shear force transmitted through the toggle joint linkage 52 to the pin 82.

FIGS. 15 through 17 illustrate a second embodiment of surgical stapler generally designated by the reference character 100 which has many parts that are essentially the same as the parts of the stapler 10 and which have been identified by the same reference numeral to which the suffix "A" has been added. Like the stapler 10, the stapler 100 includes comprises an anvil frame 12A having proximal and distal 16A ends and a pair of lateral side portions 17A and 18A that are each elongate in a longitudinal direction and spaced to define a channel therebetween. The anvil frame 12A has a handle portion (not shown but generally identical to the handle 19 of stapler 10) generally adjacent the proximal end with first and second ends, and a jaw portion 22A having specially shaped anvil surfaces 23A generally adjacent the distal end 16A. The anvil surfaces 23A are positioned in a plane generally perpendicular to the longitudinal direction. The jaw portion 22A includes surfaces defining an alignment aperture 15A opening onto the anvil surfaces 23A.

Like the stapler 10, the stapler 100 includes a cartridge assembly 32A having proximal and distal 34A ends that is mounted in the channel between the lateral side portions 17A and 18A for longitudinal movement relative to the anvil frame 12A. The cartridge assembly 32A comprises a cartridge transporting member 35A having first and second side portions that are each elongate in the longitudinal direction and that are spaced to define a ram channel therebetween. The first and second side portions have surfaces defining a cartridge groove 38A generally adjacent the distal end 34A of the cartridge assembly 32A. The cartridge groove surfaces 38A are adapted to releasably receive a cartridge housing 40A.

The cartridge housing 40A includes a plurality of staples 41A disposed in rows oriented in planes generally perpendicular to the longitudinal direction and positioned in opposition to the anvil surfaces 23A, and manually activatable means, such as a pusher 42A, for pressing the staples 41A within longitudinal slots in the cartridge housing 40A against the specially shaped anvil surfaces 23A to engage and close the staples 41A in tissue between the cartridge housing 40A and the anvil surfaces 23A. The pusher 42A has a pair of edges 43A and is positioned proximate the staples 41A for movement between pre-fired (FIG. 15) and fired (FIG. 16) positions with the pusher 42A adapted to move distally relative to the cartridge assembly 32A when the stapler 100 is fired. The cartridge housing 40A also has surfaces defining a close fitting hole or alignment through passage positioned in opposition to the alignment aperture 15A in the anvil frame 12A. The alignment through passage and the alignment aperture 15A may be generally cylindrical and coaxial.

An elongate T-bar or ram 48A is mounted in the ram channel between the first and second side portions of the cartridge transport member 35A for longitudinal movement relative to the cartridge transporting member 35A and the anvil frame 12A. The T-bar or ram 48A is adapted to drive the pusher 42A distally to eject the staples 41A from the cartridge housing 40A to press the staples 41A against the specially shaped anvil surfaces 23A and to engage and close the staples 41A in tissues between the cartridge housing 40A and the anvil jaw portion 22A when the cartridge housing 40A the anvil surfaces 23A are in the closed position.

Unlike the stapler 10, the stapler 100 includes a different means 102 for preventing the cartridge assembly 32A from moving from the open to the closed position when the stapler 100 is loaded with a cartridge housing 40A with the pusher 42A in a fired position. Like the means 80, the means 102 prevents approximation and clamping of living tissue between anvil (e.g. 23A) and cartridge (e.g. 40A) components of the stapler 100 when the stapler 100 is loaded with a spent stapler cartridge, and prevents firing of the stapler 100 when the stapler 100 is loaded with a spent stapler cartridge.

The means 102 comprises the anvil frame 12A having surfaces defining a safety aperture 103 opening into the surface of the anvil frame 12A and having a bottom surface, a locking notch 110 in the cartridge transport member 35A of the cartridge assembly 32A, and a locking plate or pin 104 having first 105 and second 106 ends.

The locking pin 104 is mounted within the safety aperture 103 for movement between a free travel position (FIG. 15) with the first end 105 of the locking pin 104 generally abutting an edge 43A of the pusher 42A and spaced from the locking notch 110 to afford a single, reciprocating movement of the cartridge assembly 32A between the open and closed positions, and a blocking position (FIG. 16) with the first end 105 of the locking pin 104 projecting beyond the safety aperture 103 and engaged with the surfaces of the locking notch 110 to prevent movement of the cartridge assembly 32A from the open to the closed position. Biasing means, such as a coil spring 109 having a first end connected to the second end 106 of the locking pin 104 and a second end connected to the bottom surface of the safety aperture 103, biases the locking pin 104 toward the blocking position.

Figure 20:
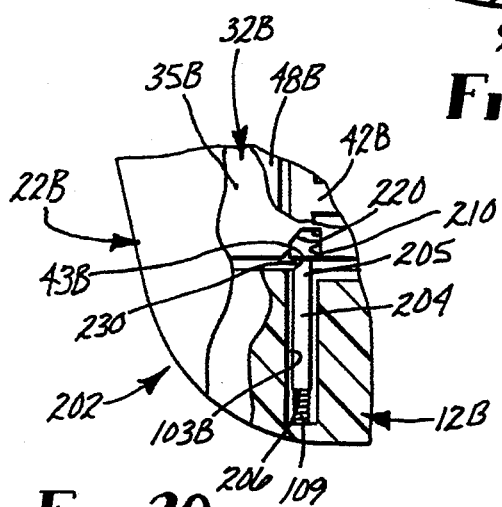
FIG. 20 is an enlarged first side view of a distal end of a third embodiment of surgical stapler according to the present invention whose proximal end is generally identical to the proximal end of the stapler of FIG. 1, with portions broken away to shown details of a ramped pin and locking notch, illustrating a pusher in a pre-fired position.
Figure 21:
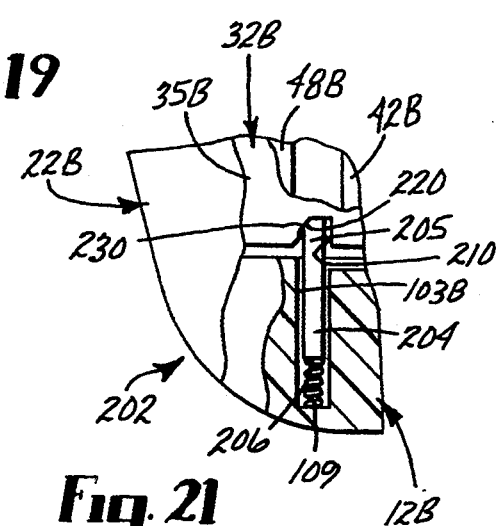
FIG. 21 is an enlarged first side view of the distal end of the stapler of FIG. 20 illustrating a pusher in a fired position.

FIGS. 20 and 21 illustrate a third embodiment of surgical stapler according to the present invention generally designated by the reference character 200 which has many parts that are essentially the same as the parts of the stapler 100 and which have been identified by the same reference numeral to which the suffix "B" has been added. Like the stapler 100, the stapler 200 includes comprises an anvil frame 12B which is elongate in a longitudinal direction. The anvil frame 12B has a handle portion (not shown but generally identical to the handle 19 of stapler 10), and a jaw portion 22B having specially shaped anvil surfaces (not shown but generally identical to the anvil surfaces 23 and 23A). The anvil surfaces are positioned in a plane generally perpendicular to the longitudinal direction. The jaw portion 22B includes surfaces defining an alignment aperture opening onto the anvil surfaces.

Like the stapler 100, the stapler 200 includes a cartridge assembly 32B that is mounted for longitudinal movement relative to the anvil frame 12B. The cartridge assembly 32B comprises a cartridge transporting member 35B surfaces defining a cartridge groove generally adjacent a distal end of the cartridge assembly 32B. The cartridge groove surfaces are adapted to releasably receive a cartridge housing (not shown but generally identical to the cartridge housings 40 and 40A).

The cartridge housing includes a plurality of staples (not shown but generally identical to the staples 41 and 41) disposed in rows oriented in planes generally perpendicular to the longitudinal direction and positioned in opposition to the anvil surfaces and manually activatable means, such as a pusher 42B, for pressing the staples within longitudinal slots in the cartridge housing against the specially shaped anvil surfaces to engage and close the staples in tissue between the cartridge housing and the anvil surfaces.

The pusher 42A has a pair of edges 43B and is positioned proximate the staples for movement between pre-fired (FIG. 20) and fired (FIG. 21) positions with the pusher 42B adapted to move distally relative to the cartridge assembly 32B when the stapler 200 is fired.

The cartridge housing also has surfaces defining a close fitting hole or alignment through passage positioned in opposition to an alignment aperture in the anvil frame 12B. The alignment through passage and the alignment aperture may be generally cylindrical and coaxial.

An elongate T-bar or ram 48B is mounted in the ram channel between the first and second side portions of the cartridge transport member for longitudinal movement relative to the cartridge transporting member and the anvil frame 12B. The T-bar or ram 48B is adapted to drive the pusher 42B distally to eject the staples from the cartridge housing to press the staples against the specially shaped anvil surfaces and to engage and close the staples in tissues between the cartridge housing and the anvil jaw portion 22B when the cartridge housing the anvil surfaces are in the closed position.

Unlike the stapler 100, the stapler 200 includes a different means 202 for preventing the cartridge assembly 32B from moving from the open to the closed position unless the stapler 200 is loaded with a ready-to-fire cartridge housing. Like the means 102, the means 202 prevents approximation and clamping of living tissue between anvil and cartridge components of the stapler 200 when the stapler 200 is unloaded or loaded with a spent stapler cartridge, and prevents firing of the stapler 200 when the stapler 200 is unloaded or loaded with a spent stapler cartridge.

Also like the means 102, the means 202 comprises the anvil frame 12B having surfaces defining a safety aperture 103B opening into the surface of the anvil frame 12B and having a bottom surface. Unlike the means 102, the means 202 includes a locking notch 210 in the cartridge transport member of the cartridge assembly 32B having sloped surfaces 220, and a locking plate or pin 204 having first 205 and second 206 ends with a ramped camming surface 230 generally adjacent the first end 205.

The locking pin 204 is mounted within the safety aperture 103B for movement between a free travel position (FIG. 20) with the first end 205 of the locking pin 204 generally abutting an edge of the pusher 42B and spaced from the locking notch 210 to afford a single, reciprocating movement of the cartridge assembly 32B between the open and closed positions, and a blocking position (FIG. 16) with the first end 205 of the locking pin 204 projecting beyond the safety aperture 103B and engaged with the surfaces of the locking notch 210 to prevent movement of the cartridge assembly 32B from the open to the closed position.

Biasing means such as a coil spring 109B having a first end connected to the second end 206 of the locking pin 204 and a second end connected to the bottom surface of the safety aperture 103B biases the locking pin 204 toward the blocking position.

Optionally, either the locking notch 210 and/or the locking pin 204 may have sloped or ramped camming surfaces to cam the locking pin 204 to the free travel position when the cartridge assembly initially moves from the open to the closed position, but which does not cam the locking pin 204 to the free-travel position when the stapler is unloaded or when the stapler is loaded with a staple cartridge other than a ready-to-fire staple cartridge.

The means 202 is believed to provide a mechanism which is easier to construct than the means 102 as the the sloped surfaces 220 and the ramped camming surface 230 are believed to be less sensitive to individual part differences or tolerances, in for example, the relative positions of the cartridge housing 40B, the cartridge transport member 35B and the edge 43B of the pusher 42B.

The present invention has now been described with reference to several embodiments thereof. It will be apparent to those skilled in the art that many changes can be made in the embodiment described without departing from the scope of the present invention. For example, the pin 82 and the spring 86 may be replaced with a plastic part with an integrally molded spring. Also, the pin 104 may be adapted to engage a slot (not shown) in the cartridge housing 40A rather than the locking notch 110 in the cartridge assembly 32. Additionally, the means 94 could be completely eliminated from the stapler 10 according to the present invention, and the anvil frame 12 and the cartridge assembly 32 may be constructed from any suitable material such as but not limited to a metal or plastic material. Moreover, the locking plate or pins 82, 104, 204 may be constructed from any suitable, tough material such as metal or plastic and may have arcuate portions (not shown) adjacent their ends which are adapted to engage the edge (e.g. 43B) of the pusher. The arcuate edges cam the pins toward the free travel position when the stapler is loaded with an unfired cartridge and the cartridge assembly initially moves toward the closed position. Thus the scope of the present invention should not be limited to the structure described in this application, but only by structures described by the language of the claims and the equivalents of those structures.

What is claimed:

1. A surgical stapler comprising:
an anvil frame having proximal and distal ends, and a pair of lateral side portions each being elongate in a longitudinal direction and spaced to define a channel therebetween, said anvil frame having a handle portion generally adjacent said proximal end and having first and second ends, and a jaw portion having anvil surfaces generally adjacent said distal end and positioned in a plane generally perpendicular to said longitudinal direction, and an elongate manually movable lever part having first and second ends, said lever part having pivot means at said second end adapted for affording relative pivotal movement of said lever part and said anvil frame between a release position with said first end of said lever part being spaced from said first end of said handle portion and an actuation position with said lever part and said handle portion in closely spaced relationship;

biasing means for biasing said lever part toward said release position;

a cartridge assembly having proximal and distal ends and being mounted in said channel between said lateral side portions for longitudinal movement relative to said anvil frame, said cartridge assembly including, a cartridge transporting member having first and second side portions each being elongate in said longitudinal direction and being spaced to define a ram channel therebetween, said first and second side portions having surfaces defining a cartridge groove generally adjacent said distal end of said cartridge assembly, said cartridge groove surfaces being adapted to releasably receive a cartridge housing containing a plurality of staples disposed in at least one row positioned in opposition to said anvil surfaces, and pusher means for pressing said staples within said cartridge housing against said anvil surfaces to engage and close the staples in tissue between the cartridge housing and the anvil surfaces, said pusher means mounted for movement relative to the cartridge housing between a pre-fired and a fired position;

means mounting said cartridge assembly for longitudinal movement relative to said anvil frame between a closed position with said cartridge housing and said anvil surfaces in closely spaced relationship, and an open position with said cartridge housing and said anvil surfaces spaced farther from each other than in said closed position;

an elongate ram mounted in said ram channel between said first and second side portions for longitudinal movement relative to said cartridge transporting member and said anvil frame, said ram engaging said pusher means to move said pusher means from said prefired position to said fired position when said cartridge housing and said anvil surfaces are in closely spaced relationship;

actuation means for initially moving said cartridge assembly from said open position to said closed position in response to movement of said lever part from said release position to said actuation position and for subsequently moving said ram distally relative to said cartridge transporting member by again moving said lever part from said release position to said actuation position;

means for biasing said cartridge assembly from said closed position to said open position; and means for preventing said cartridge assembly from moving from said open position to said closed position when the stapler is loaded with a cartridge housing having the pusher means disposed in a fired position, said preventing means including a safety aperture defining an opening in the surface of the anvil frame and a locking pin mounted in the safety aperture for movement between a first position to afford free movement of the cartridge assembly between said open position and said closed position, and a second blocking position to prevent such movement.

2. A surgical stapler according to claim 1, wherein said pusher means comprises a pusher having a pair of edges and being positioned proximate the staples for movement between said pre-fired and said fired positions with the pusher adapted to move distally relative to said cartridge housing when the stapler is fired, and said locking pin abutting an edge of said pusher in said first position to afford a single, reciprocating movement of said cartridge assembly between said open and closed positions, and projecting beyond the safety aperture in said second position to prevent movement of said cartridge assembly from said open to said closed position, and biasing means for biasing said locking pin toward said blocking position.

3. A surgical stapler according to claim 2, wherein said biasing means for biasing said locking pin toward said blocking position comprises a coil spring having a first end connected to a second end of said locking pin and a second end connected to a bottom surface of said safety aperture.

4. A surgical stapler according to claim 2, wherein said locking pin has a ramped camming surface generally adjacent its first end.

5. A surgical stapler according to claim 1, wherein said actuation means comprises a toggle joint linkage having an over center pivoting portion and first and second ends with the first end fixed to said anvil frame and with the second end connected to said cartridge transporting member, said over center pivoting portion having surfaces adapted to engage said lever part when said lever part is first moved from said release to said actuation position to move said toggle joint linkage from a retracted position with the cartridge assembly in said open position toward an extended position to drive said cartridge assembly from said open to said closed positions, means for retaining said cartridge assembly in said closed position against the bias of said means for biasing said cartridge assembly from said closed to said open position, surfaces defining a cam shoulder surface on said ram, and a pawl having first and second ends and a cam surface generally adjacent the second end, and means mounting said pawl on said lever part for movement between a first position with the cam surface being spaced from the cam shoulder surface on said ram and a second position with the cam surface engaged with the cam shoulder surface on said ram to afford firing of said stapler by driving said ram distally relative to said cartridge transporting member by moving said lever part from said release to said actuation positions a second time.

6. A surgical stapler according to claim 5, wherein said stapler further includes means for biasing said pawl toward said second position, and said ram has surfaces adapted to retain said pawl in said first position until said cartridge assembly is moved from said open to said closed position.

7. A surgical stapler according to claim 5, wherein said stapler further includes a release arm having a first end pivotally mounted to the proximal end of said anvil frame and a second engagement end, said release arm having surfaces adapted to engage said pawl and said toggle joint linkage to move said pawl from said second to said first position and to move said toggle joint linkage from said extended toward said retracted position to afford movement of said cartridge assembly from said closed to said open position under the bias of said means for biasing said cartridge assembly from said closed to said open position.

8. A surgical stapler comprising:
an anvil frame elongate in a longitudinal direction and having proximal and distal ends, and a jaw portion having anvil surfaces generally adjacent said distal end and positioned in a plane generally perpendicular to said longitudinal direction,
an elongate manually movable lever having pivot means for affording relative pivotal movement of said lever and said anvil frame between a release position with one end of said lever being spaced from said proximal end of said anvil frame and an actuation position with said lever and said anvil frame in closely spaced relationship;
a cartridge assembly having proximal and distal ends and being mounted adjacent said anvil frame for longitudinal movement relative to said anvil frame, said cartridge assembly including, a cartridge transporting member having surfaces defining a cartridge groove generally adjacent said distal end of said cartridge assembly, said cartridge groove surfaces being adapted to releasably receive a cartridge housing containing a plurality of staples disposed in at least one row positioned in opposition to said anvil surfaces, and pusher means for pressing said staples within said cartridge housing against said anvil surfaces to engage and close the staples in tissue between the cartridge housing and the anvil surfaces, said pusher means mounted for movement relative to said cartridge housing between a pre-fired position and a fired position;
means mounting said cartridge assembly for longitudinal movement relative to said anvil frame between a closed position with said cartridge housing and said anvil surfaces in closely spaced relationship, and an open position with said cartridge housing and said anvil surfaces spaced farther from each other than in said closed position;
an elongate ram mounted for longitudinal movement relative to said cartridge transporting member and said anvil frame, said ram being engaging the pusher means when said cartridge housing and said anvil closed position;
actuation means operable in a first movement to initially move said cartridge assembly from said open position to said closed position in response to movement of said lever from said release to said actuation position and operable in a second movement to subsequently move said ram distally relative to said cartridge transporting member by again moving said lever from said release to said actuation positions; and
means for preventing said cartridge assembly from moving from said open to said closed positions when the stapler is loaded with a cartridge housing having a pusher means in a fired position, said preventing means including a safety aperture defining an opening in the surface of the anvil frame and a locking pin mounted in the safety aperture for movement between a first position to afford free movement of the cartridge assembly between said open position and said closed position, and a second blocking position to prevent such movement.

9. A surgical stapler according to claim 8, wherein said pusher means comprises a pusher having a pair of edges and being positioned proximate the staples for movement between said pre-fired and said fired positions with the pusher adapted to move distally relative to said cartridge housing when the stapler is fired, and said locking pin abutting an edge of said pusher in said first position to afford a single, reciprocating movement of said cartridge assembly between said open and closed positions, and projecting beyond the safety aperture in said blocking position to prevent movement of said cartridge assembly from said open to said closed position, and
biasing means for biasing said locking pin toward said blocking position.

10. A surgical stapler according to claim 9 wherein said biasing means for biasing said locking pin toward said blocking position comprises a coil spring having a first end connected to a second end of said locking pin and a second end connected to a bottom surface of said safety aperture.

11. A stapler according to claim 9 wherein said cartridge assembly includes surfaces defining a locking notch, and, in the blocking position, said locking pin projects beyond the safety aperture and engages with the surfaces of the locking notch to prevent movement of the cartridge assembly from the open to the closed position.

12. A stapler according to claim 11 wherein said locking notch includes a sloped surface.

13. A stapler according to claim 11 wherein said locking pin includes a ramped camming surface.

14. A locking device for a surgical fastener applying instrument, said instrument including a first jaw member having a cartridge containing a plurality of fasteners and a second jaw member, advancing means for approximating said first jaw member towards said second jaw member to grip tissue therebetween, and means for driving said fasteners from said cartridge into said tissue, said locking device comprising:
means for engaging said first jaw member, said engaging means positioned on said second jaw member and mounted for movement from a non-engaged position prior to said fasteners being driven from said cartridge to an engaged position subsequent to said fasteners having been driven from said cartridge, said engaging means in said engaged position impeding distal movement of said first jaw member, said engaging means mounted for movement to said engaged position only after said fasteners have been driven from said cartridge.

15. In an apparatus for applying a plurality of surgical fasteners to body tissue, said apparatus including a first jaw member having a cartridge containing a plurality of fasteners positioned thereon and a second jaw member, advancing means for approximating said first jaw member towards said second jaw member to grip tissue therebetween, and means for driving said fasteners into said tissue, the improvement which comprises:
means positioned on said second jaw member for engaging said first jaw member, said engaging means mounted for movement from a non-engaged position prior to said fasteners being driven from said cartridge to an engaged position subsequent to driving said fasteners, said engaging means in said engaged position impeding distal movement of said first jaw member after said fasteners have been driven from said cartridge, said engaging means being disengaged from said first jaw member when said cartridge contains said plurality of fasteners.

16. A surgical stapler comprising:
a handle assembly;
an elongated frame extending from the handle assembly and having a longitudinal axis;
an anvil disposed at the distal end of the elongated frame and oriented perpendicular to the longitudinal axis;
a cartridge assembly operatively associated with the elongated frame and housing a plurality of surgical staples for application to body tissue;
an actuation mechanism actuable from the handle assembly for effecting relative movement of the cartridge assembly and the anvil between open and closed positions; and
a blocking mechanism mounted to said frame for movement between a non-blocking position and a blocking position to engage the cartridge assembly and thereby prevent relative movement of the cartridge assembly and the anvil to the closed position after the staples have been fired from the cartridge.

17. A surgical stapler as recited in claim 16, wherein the blocking mechanism interacts with the cartridge assembly.

18. A surgical stapler as recited in claim 17, wherein the blocking mechanism extends into the cartridge assembly in the blocking position.

19. A surgical stapler as recited in claim 18, wherein the cartridge assembly defines a notched area configured to receive the blocking mechanism in the blocking position.

20. A surgical stapler as recited in claim 18, wherein the blocking mechanism comprises a cylindrical shaft slidable between non-blocking and blocking positions.

21. A surgical stapler as recited in claim 18, wherein the blocking mechanism comprises a rectangular blocking plate.

22. A surgical stapler as recited in claim 21, wherein the notched area includes an inclined surface and the blocking plate includes an inclined edge for abutting the inclined surface.

23. A surgical stapler as recited in claim 16, further comprising biasing means for urging the blocking mechanism toward the blocking position.

24. A surgical stapler as recited in claim 16, further comprising a cartridge transport member operatively associated with the frame for transporting the cartridge assembly between the open and closed positions.

25. A surgical stapler as recited in claim 24, wherein the cartridge assembly is removable from the cartridge transport member.

26. A surgical stapler as recited in claim 24, wherein the blocking mechanism is mounted on the frame and engages the cartridge transport member in the blocking position.

27. A surgical stapler as recited in claim 26, wherein the blocking mechanism comprises a shaft slidable in a direction perpendicular to the longitudinal axis.

28. A surgical stapler as recited in claim 16, wherein the cartridge assembly includes a staple pusher, the staple pusher biasing the blocking mechanism to the non-blocking position when the cartridge assembly contains staples.

29. A surgical stapler as recited in claim 28, wherein firing of the staples moves the staple pusher distally to allow the blocking mechanism to move to the blocking position.

30. A surgical stapler as recited in claim 29, wherein the blocking mechanism is spring biased toward the blocking position.

31. A surgical stapler as recited in claim 16, wherein the frame includes an aperture and the blocking mechanism is slidably positioned in the aperture.

32. A surgical stapler comprising:
an elongated frame having a longitudinal axis;
an anvil disposed at the distal end of the elongated frame and oriented perpendicular to the longitudinal axis;
a cartridge containing a plurality of surgical staples, the cartridge being movable toward the anvil from a proximal position to a clamping position to clamp tissue against the anvil;
a driving mechanism for firing the staples from the cartridge in a direction substantially parallel to the longitudinal axis;
a locking mechanism positioned in the frame, the locking mechanism movable between a non-locking position allowing movement of the cartridge to the clamping position and a locking position preventing movement of the cartridge to the clamping position, the cartridge urging the locking mechanism to the non-locking position when loaded with staples.

33. A surgical stapler as recited in claim 32, further comprising biasing means for urging the locking mechanism toward the locking position.

34. A surgical stapler as recited in claim 32, wherein the locking mechanism comprises a shaft slidable in a direction perpendicular to the longitudinal axis of the frame.

35. A surgical stapler as recited in claim 34, wherein the cartridge defines a notched area configured to receive the shaft in the locking position.

36. A surgical stapler as recited in claim 32, wherein the locking mechanism comprises a rectangular blocking plate.

37. A surgical stapler as recited in claim 36, wherein the cartridge defines a notched area having an inclined surface and the blocking plate includes an inclined edge for abutting the inclined surface in the locking position.

* * * * *